US006379696B1

United States Patent
Asmussen et al.

(10) Patent No.: US 6,379,696 B1
(45) Date of Patent: *Apr. 30, 2002

(54) THERAPEUTIC PREPARATION FOR THE TRANSDERMAL ADMINISTRATION OF ACTIVE SUBSTANCES

(75) Inventors: Bodo Asmussen, Bendorf-Sayn; Andreas Koch, Neuwied; Rudolf Matusch, Marburg, all of (DE)

(73) Assignee: LTS Lohmann Therapie-System Gmbh (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,326

(22) PCT Filed: Sep. 21, 1996

(86) PCT No.: PCT/EP96/04138

§ 371 Date: May 5, 1998

§ 102(e) Date: May 5, 1998

(87) PCT Pub. No.: WO97/17061

PCT Pub. Date: May 15, 1997

(30) Foreign Application Priority Data

Nov. 6, 1995 (DE) .......................................... 195 41 260

(51) Int. Cl.[7] .............................. A61F 13/00; A61K 9/70

(52) U.S. Cl. ...................... 424/449; 424/94.4; 424/443; 424/449

(58) Field of Search ................................ 424/94.4, 443, 424/43, 444, 447, 449; 514/946, 969, 947

(56) References Cited

U.S. PATENT DOCUMENTS

| 5,211,947 A | * | 5/1993 | Brannan et al. .......... 424/94.63 |
| 5,240,932 A | * | 8/1993 | Morimoto et al. .......... 514/282 |
| 5,316,765 A | * | 5/1994 | Folkers et al. ............. 424/94.1 |
| 5,770,220 A | * | 6/1998 | Meconi et al. .............. 424/448 |
| 5,968,983 A | * | 10/1999 | Kaesemeyer ................ 514/564 |

FOREIGN PATENT DOCUMENTS

DE 3634016 * 10/1987

OTHER PUBLICATIONS

Ehrhardt Proksch, Lipidsenker-induzierte Nebenwirkungen an der Haut, *Hautarzt* 46: 76–80, 1995.

* cited by examiner

*Primary Examiner*—Thurman K. Page
*Assistant Examiner*—S. Howard
(74) *Attorney, Agent, or Firm*—Ann W. Speckman; Jim Klaniecki

(57) ABSTRACT

A therapeutic preparation for the transdermal application of active substances through the skin comprising additives causing an increase in the percutaneous absorption rate of active substances which can normally only insufficiently be absorbed transdermally is characterized by the fact that the additives are HMG-CoA-reductase-inhibitors.

3 Claims, 2 Drawing Sheets

THERAPEUTIC PREPARATION FOR THE TRANSDERMAL ADMINISTRATION OF ACTIVE SUBSTANCES

Figure 1:
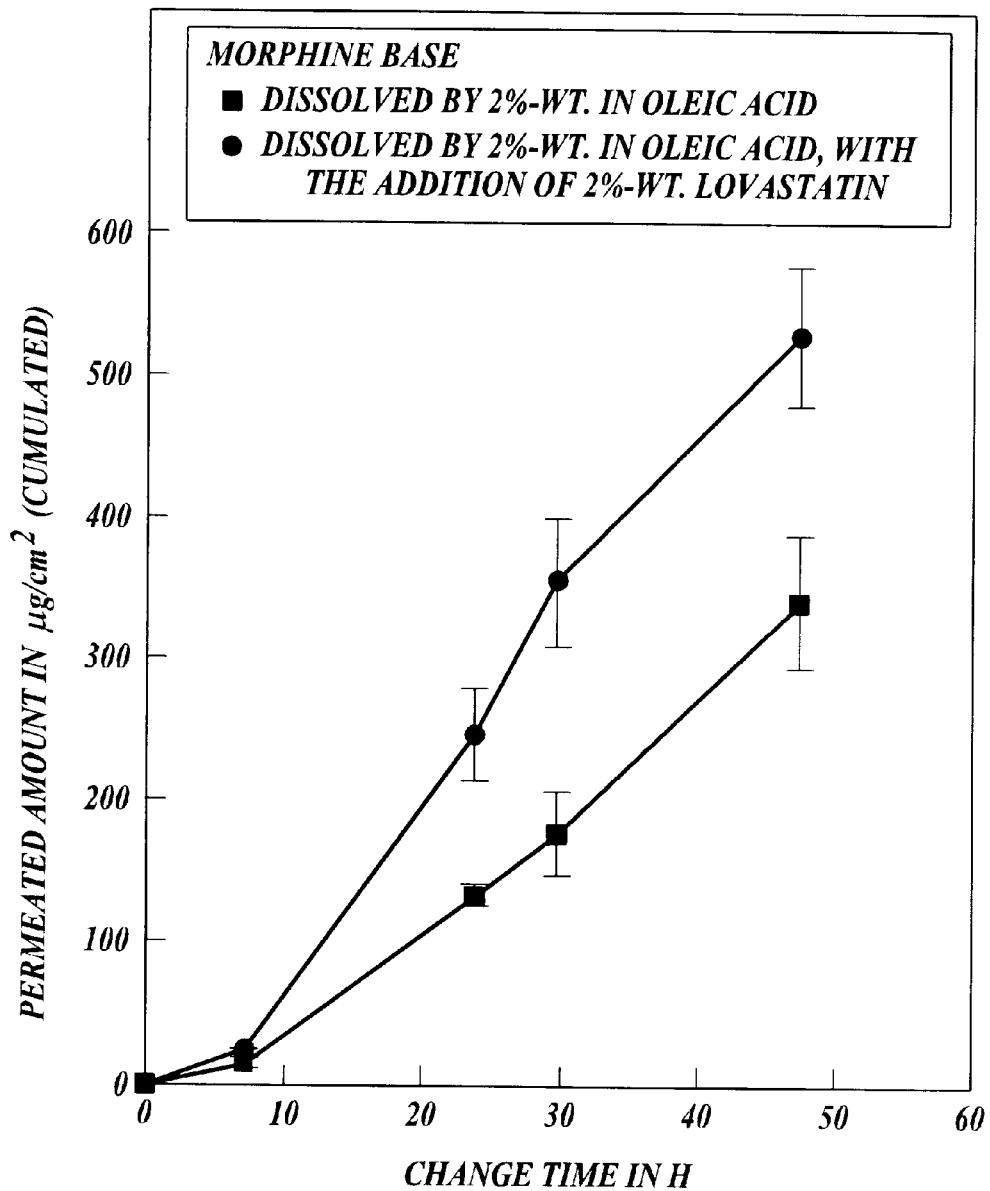

The present invention relates to a therapeutic preparation for the transdermal application of active substances through the skin comprising additives causing an increase in the percutaneous absorption rate of active substances which can normally only insufficiently be absorbed transdermally.

One of the major problems of administration forms comprising percutaneously absorbable active substances, for example, transdermal therapeutic systems, is to overcome the skin's natural permeability barrier. It serves the epidermal protective function of the skin and is formed by wide laminated lipid bilayers in the intercellular spaces of the epidermis, it is a barrier resisting any attempt of percutaneous absorption.

In order to overcome this problem, permeation-promoting additives, so-called classical enhancers, have already been added to therapeutic preparations for the transdermal application of active substances for some time now. These enhancers increase the percutaneous absorption rate of lipophilic or hydrophilic medicinal substances over a longer period of time. However, it turned out that a number of active substances nevertheless have an insufficient percutaneous absorption rate. Occasionally, the area of a transdermal therapeutic preparation has been enlarged to achieve a therapeutically effective active substance flow through the skin into the organism. However, this also results in a number of disadvantages; on the one hand, such a patch becomes unnecessarily expensive both with respect to costs and production and, on the other hand, patients find a large transdermal patch disagreeable. When a larger skin area is covered, partial detachment of the patch may easily occur through play of muscles or other movements of the body, this impairs the controlled active substance flow to a considerable extent.

The mode of action of classical enhancers has not yet been researched down to the last detail. However, the enhancers conventionally used today are attributed physicochemical mechanisms of action; for example, an increase of the lipid solubility through modified distribution coefficients of the active substance in the epidermal lipid bilayers, or a reduction of the diffusion coefficient owing to an entropy decrease in the liquid-crystalline condition of the cutaneous lipids through steric effects and polar interactions between enhancer and cutaneous lipid.

Furthermore, it is known that the structure of the skin can also be modified by the fact that a direct intervention in biochemical regeneration processes, for example in the epidermis, influences the permeability barrier of the skin. For example, a work of Proksch (J. Hautarzt, 1955, V. 46 N 2, pp. 76–80) describes that the topical application of the specific HMG-CoA-inhibitor LOVASTATIN results in a decrease of the cholesterol level in the skin with a simultaneous increase in the transepidermal loss of water and the DNA-synthesis in the epidermis; this disturbs the natural permeability barrier of the skin.

The use of lipid-lowering substances in transdermal therapeutic systems is mentioned in DE 36 34 016. However, this specification of lipid-lowering substances in combination with other active substances exclusively serves therapeutic objectives; it is not intended to increase the percutaneous absorption rate of active substances which can normally only insufficiently be absorbed transdermally.

It is the object of the present invention to advance a therapeutic preparation of the kind mentioned in the introductory part of claim 1 and to improve it in such a manner that it changes the structure of the skin to such an extent that an increased absorption of medicinal agents is achieved as a result of a reduced diffusion resistance of the skin, in particular of the epidermis, so that even active substances that can normally only insufficiently be absorbed have a considerably improved rate of permeation.

In order to achieve this object, the present invention proposes that the additives to increase the percutaneous absorption rate of a preparation be HMG-CoA-reductase-inhibitors. Thus, the effect mentioned in the work of Proksch, i.e., a disturbance of the skin's natural permeability barrier—which, according to this publication, exclusively serves therapeutic purposes by combining lipid-lowering substances with other active substances—is selectively used to increase the percutaneous absorption rate of lipophilic or hydrophilic medicinal agents over a longer period by using HMG-CoA-reductase-inhibitors with at least 0.1 but a maximum of 20%-wt. as permeation-promoting additives.

In contrast to classical enhancers, the present invention is based on a biochemical principle of action with respect to the surprisingly achieved permeation promotion. With a disturbed permeability barrier in the epidermis, this principle forms a "window" over a longer period through which medicinal agents being problematic owing to their physico-chemical properties, for example, having molecular masses of more than 400 dalton, a high melting point, low water-solubility or a low distribution coefficient, water/oil, can actually overcome, in fact with added force, the skin passage transdermally.

The suppression of the epidermal biolipid synthesis which is caused by HMG-CoA-reductase-inhibitors also prevents that natural repair mechanisms of the epidermis to restore a disturbed permeability barrier, which are usual when enhancers having fat-soluble properties are used, fail to succeed. For this reason, the permeation-promoting effect, the so-called "window" within the permeability barrier, is of longer duration and thus also of practical significance in the transdermal therapy of medicinal substances.

The problem of skin-irritating side effects, which prevent the practical use of many potential enhancers and in particular also apply to HMG-CoA-reductase-inhibitors, such as LOVASTATIN, is qualified according to the present invention by the fact that a maximum of 20%-wt. of the possible lipid-lowering substances are used in transdermal application systems (TTS, ointments, or pastes).

Figure 2:
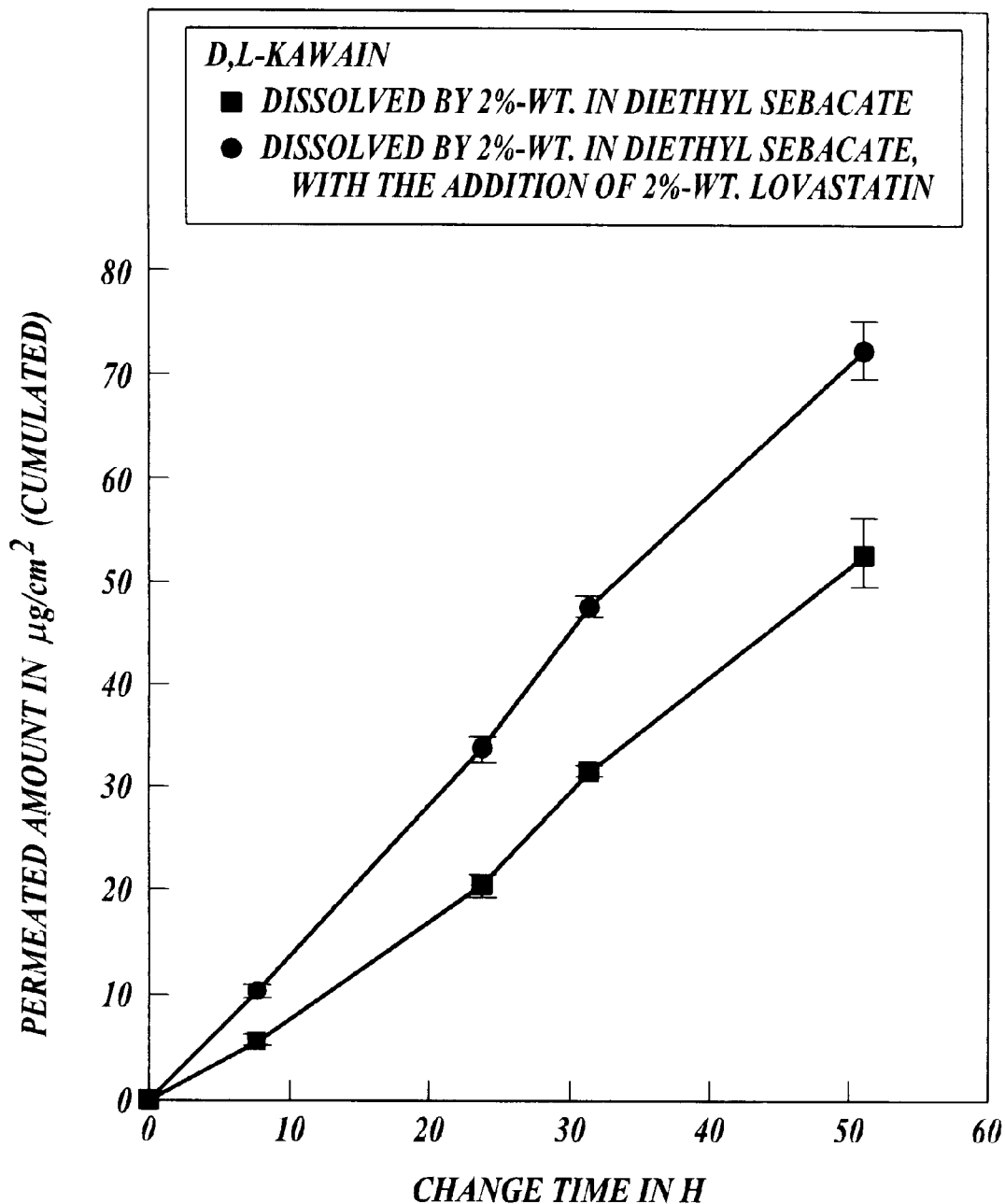

The present invention will be illustrated by means of the measuring results shown in FIGS. 1 and 2.

Examples of normally insufficiently absorbable active substances, in addition to morphine, include: theophylline, L-thyroxine, ergotamine, D, L-kawain, D, L-warfarin.

FIG. 1 shows the influence of the lipid-lowering substance LOVASTATIN on the permeation rate of morphine base, using excised guinea pig skin
(released in 0.9% salt solution at T=37° C., n=3, +/−SD)

The example proves that the addition of the lipid-lowering substance LOVASTATIN, even in small amounts (2%-wt.), can double the permeation rate after 24 h.

An increase is maintained even beyond this period (up to 48 h) with about 80%.

FIG. 2 shows the influence of the lipid-lowering substance LOVASTATIN on the permeation rate of D,L-kavain , using excised guinea pig skin
(released in isotonic phosphate buffer pH 7.4 at T=37° C., n=3, +/−SD)

The example proves that the addition of the lipid-lowering substance LOVASTATIN, even in small amounts (2%-wt.), can achieve an increase in the permeation rate of an active substance that is poorly absorbable transdermally by 70% after 24 h.

An increase is maintained even beyond this period (up to 52 h) with 50%.

We claim:

1. A method for increasing the percutaneous absorption rate of one or more active substances which can normally only insufficiently be absorbed transdermally, comprising administering an active substance and an additive through the skin, wherein the active substance is a drug substance selected from the group consisting of morphine base, theophyline, L-thyroxine, ergotamine, D,L-kavain and D,L-warfarin, and the additive comprises an HMG-CoA-reductase inhibitor contained within the transdermal therapeutic system in a controlled release form, thereby achieving a therapeutically effective active substance flow through the skin while avoiding skin irritating side effects.

2. The method according to claim 1, wherein the additive is selected for the group consisting of LOVASTATIN, SIMVASTATIN, MEVASTATIN, and PROVASTATIN.

3. The method according to claim 1, wherein the portion of the HMG-Co-A-reduictase-inhibitors amounts to at least 0.1 and a maximum of 20%-wt.

* * * * *

UNITED STATES PATENT AND TRADEMARK OFFICE
CERTIFICATE OF CORRECTION

PATENT NO. : 6,379,696 B1  Page 1 of 1
DATED : April 30, 2002
INVENTOR(S) : Bodo Asmussen, Andreas Koch and Rudolf Matusch It is certified that error appears in the above-identified patent and that said Letters Patent is hereby corrected as shown below:

<u>Column 4,</u>
Line 10, replace "HMG-CO-A-reduictase-inhibitors" with -- HMG-CO-A-reductase-inhibitors --

Signed and Sealed this

Fourth Day of March, 2003

JAMES E. ROGAN
*Director of the United States Patent and Trademark Office*